United States Patent [19]
Anderson

[11] 3,980,431
[45] Sept. 14, 1976

[54] MOBILE LOADING MEANS FOR STERILIZERS

[75] Inventor: Edgar L. Anderson, Penfield, N.Y.

[73] Assignee: Sybron Corporation, Rochester, N.Y.

[22] Filed: Sept. 24, 1971

[21] Appl. No.: 183,699

Related U.S. Application Data

[63] Continuation of Ser. No. 64,146, Aug. 3, 1970, abandoned, which is a continuation of Ser. No. 654,147, July 18, 1976, abandoned.

[52] U.S. Cl................................. 21/91; 21/94; 21/103; 21/105; 214/16 B; 214/38 BB
[51] Int. Cl.².................. A61L 3/02; B65G 65/00
[58] Field of Search.............. 21/96, 105, 91–94, 21/95, 97, 98, 103; 214/16 B, 16.4 R, 38 B, 38 BA; 105/366 R; 206/45.16, 46; 312/317 A, 33

[56] References Cited
UNITED STATES PATENTS

| | | | |
|---|---|---|---|
| 755,089 | 3/1904 | Wercel | 312/333 |
| 1,288,462 | 12/1918 | Alborn | 214/38.20 |
| 1,900,832 | 5/1933 | Bales et al. | 312/333 |
| 1,923,785 | 8/1933 | Holan | 105/366 |
| 2,036,336 | 4/1936 | Kellett | 105/366 |
| 2,146,436 | 2/1939 | Lima | 105/366 |
| 2,147,236 | 2/1939 | Biggs | 21/105 |
| 2,150,371 | 3/1939 | Furnish | 214/38.22 |
| 3,180,281 | 4/1965 | Sherrie et al. | 214/38.22 |
| 3,182,607 | 5/1965 | Sherrie | 105/366 |
| 3,368,865 | 2/1968 | Schuck | 21/96 |

Primary Examiner—Morris O. Wolk
Assistant Examiner—Bradley Garris
Attorney, Agent, or Firm—Schovee & Boston

[57] ABSTRACT

A sterilizer vessel 1 is mounted in a pit defining an open channel formed between the edges 12 and 14 of the room floor and sterilizer floor respectively. A mobile unit 18 has a leading edge having an elevating cam surface 34 and extending sufficiently forward of the lead caster 26, thereby to be supportingly engaged by an anti-friction supporting element 30 internally of the vessel 1 before the lead caster passes over the open channel.

4 Claims, 1 Drawing Figure

U.S. Patent  Sept. 14, 1976  3,980,431
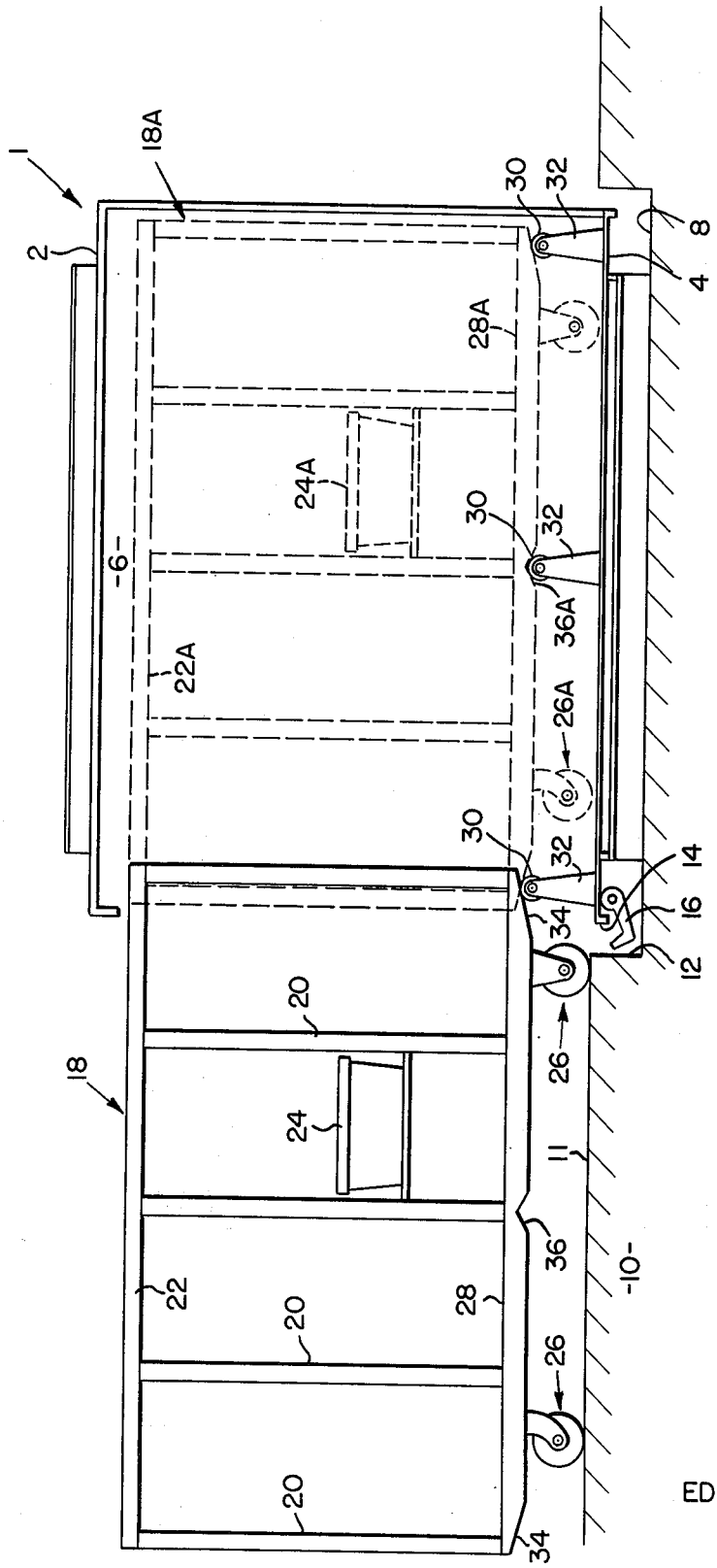
INVENTOR
EDGAR L. ANDERSON
BY Thomson & Schouee
ATTORNEY

MOBILE LOADING MEANS FOR STERILIZERS

CROSS-REFERENCES TO RELATED APPLICATIONS

This application is a continuation of my copending application Ser. No. 64,146, filed Aug. 3, 1970 and now abandoned, which was a streamlined continuation of my application Ser. No. 654,147, filed July 18, 1967 and now abandoned.

SUMMARY OF THE INVENTION

A vessel 1 having top 2, bottom 4 and sidewalls 6, first support means 30 and 32 adapted to support the hereinafter defined mobile unit 18 internally of vessel 1, a mobile unit 18 adapted to be received in the vessel 1 and having casters 26 adapted to roll on a room floor and having a second support means 28 adapted to be received by the first support means 30, and 32 internally of said vessel. The second support means having a forward projection adapted to be received by the first support means 30 and 32, while said mobile unit 18 is being supported by the casters 26 on the room floor externally of said vessel 1.

It has long been a problem to load and unload goods to be sterilized into the sterilizing chamber. Various solutions to the problem have been sought and discovered, but to my knowledge no one has devised as satisfactory and simple a solution as revealed by this invention. Heretofore, it has been known to provide a sterilizer in a pit so that the floor of the sterilizer is at substantially the same level as the floor of the room in which the sterilizer is mounted. However, the sterilizer door requires that there be an open channel in front of the door adapted to receive the door; in the past a ramp has been provided across that channel in order that a mobile unit may be received inside the sterilizer. As a solution to the problem I provide the combination of: sterilizing vessel mounted in a pit such that the floor of the sterilizing vessel is substantially at the level of the floor of the room in which the vessel is mounted; supporting structure mounted inside of the vessel preferably including a plurality of anti-friction rollers mounted along the sidewalls of the sterilizing vessel for movably supporting a track or supporting element mounted along each of corrsponding side edges of a mobile unit adapted to be received internally of the vessel; and a forward projection on the mobile unit adapted to be received by the supporting structure of the vessel while the mobile unit is still being supported on the floor externally of the vessel, thereby to provide uninterrupted support of the mobile unit as it is being received in the vessel without any ramp or other auxiliary structure.

It is of particular significance that I provide an elevating cam surface on either the supporting structure internally of the vessel or on the supporting element or track of the mobile unit, or some other suitable means to elevate the casters of the mobile unit off of the floor of the sterilizing vessel so that during sterilization under pressure, the tires of the casters are not resting on the floor of the sterilizer and therefore not subject to flattening. Therefore, it is the primary object of my invention to provide an improved combination of sterilizing vessel and mobile unit facilitating egress and ingress of the mobile unit, and articles carried thereon to be sterilized.

Other objects and advantages of this invention will be particularly set forth in the claims and will be apparent from the following description of the drawing in which the FIGURE is a solid line diagrammatic side elevational view with the sterilizing vessel in cross section of one embodiment of my invention with the mobile unit illustrated in an alternative position in the broken line position.

In the drawing, I illustrate a sterilizing vessel generally indicated by the numeral 1, having a top wall 2, a bottom wall or floor 4, and a pair of sidewalls only one of which is illustrated at 6. The sterilizing vessel 1 is mounted in a pit 8 provided in a concrete or other suitable floor 10. There is an open channel defined between an edge 12 of the room floor 10 and a forward edge 14 of the sterilizer. In the past, a ramp has been provided extending between these two edges in order that the mobile units may be transported into the sterilizing vessel.

In the past when mobile units have been utilized for transporting goods into and out of a sterilizing vessel it has been necessary to provide a ramp for either elevating the mobile units into the sterilizers if it is a floor mounted sterilizer with the floor above room floor or a ramp from the floor over to the sterilizer if there is an open channel between the two by reason of the sterilizer being mounted in a pit so that the floor of the sterilizer is at substantially the level of the floor in the room in which the sterilizer is mounted.

It is necessary to provide such a channel for a sterilizing vessel when the vessel is to be mounted below room level in a pit because the channel is adapted to receive the door of the sterilizing vessel. With this kind of a construction it is essential that the lower edge of the door is lower than the floor. I have not herein attempted to illustrate any particular type of door adapted for closure of the vessel 1, since the type of door is not essential to the concept of my invention; but rather it will be understood that any type of a sterilizing door which is mounted in the manner suitable for the illustrated sterilizing vessel would be acceptable. I have chosen to illustrate a locking hook 16 adapted for embracing the outer edge of the sterilizing door for locking it in the manner described in my U.S. Pat. No. 3,145,021, with reference to the hook element 42 described in that patent. It will be understood with reference to the latter referred to patent, that a plurality of such locking elements 16 are provided in spaced positions around the entire periphery of the door and mounted on the sterilizer for locking the door shut. However, this type of locking mechanism is not essential to the concept of my invention.

I provide a mobile unit or rack generally indicated by the numeral 18 which may be constructed in any suitable manner, as for example, by interconnected vertical and horizontal channel bar stock members 20 and 22 respectively providing rigid support for baskets 24 or other goods to be retained thereon; and the mobile unit is supported by a plurality of four swivel caster units 26. Basically, such constructions are well-known. Along opposing sides of the mobile unit 18, I provide track or support elements 28 forming the bottom edge along two longitudinal sides of the mobile unit. Each support element or track element 28 may comprise either a channel-shaped member extending along only each side of the mobile unit 18 adapted to receive or pass over the hereinafter described rollers 30. Or, the tracks 28 may comprise the entire bottom surface extending across the mobile unit 18. The internal dimensions of the vessel 1 and exterior dimensions of the mobile unit 18 are such that the mobile unit 18 is conveniently received internally of the vessel 1 as shown in broken lines at 18A in which position the tracks 28 are supported on a plurality of anti-friction roller supporting elements 30 mounted internally of the vessel on support pedestals 32 along the sidewall 6 and the opposing sidewall (not shown) in a manner suitable for suspending the entire mobile unit 18 when received internally of the vessel 1 as shown in broken line. Thus, only one side of the mobile unit 18 and vessel 1 need by shown since the other side is identical, and the FIGURE can be considered also to be a view of the other side since the other side is simply a mirror image of the side shown. In the broken line position, parts corresponding to the solid line position are designated by the same numeral followed by the suffix A. In this position, the caster shown at 26A is suspended in non-engaging relationship with the floor or bottom wall 4 of the vessel 1. In the illustrated embodiment, the bottom wall 4 is only slightly, i.e., approximately one-quarter of an inch lower than the upper surface 11 of the room floor 10. However, it will be understood that the height of the anti-friction roller supporting elements 30 and casters 26 and the elevational rise of an elevating cam surface 34 on the leading edge of the track 28 would all be coactively designed such that the casters 26 preferably do not engage the floor 4 of the vessel 1. It will be understood, that the level of the sterilizer floor 4 could be at or above the upper level 11 of the room floor 10 and still fulfill this desired result.

The forward projection or leading portion of the mobile unit 18 extending between the leading caster 26 and the leading edge of the mobile unit being received into the vessel first, is of significant importance to my invention. First of all, it is of sufficient length to be received on the left hand, as viewed in reference to the FIGURE, anti-friction support element or roller 30 while the leading caster 26 is engaging the upper surface 11 of the room floor 10. In this manner, the leading edge of the mobile unit 18 is picked up by the left-hand support elements 30 before the leading caster 26 passes over the open channel formed between the edges 12 and 14 of the floor and vessel respectively, thereby suspending the caster as it passes over the open channel of the pit 8.

It is also of significant importance to provide the elevating cam surface 34 at the leading edge of the mobile unit 18 in order to provide the smoothest transfer of the mobile unit from the room floor into the vessel 1. Also, this combination functions to elevate the mobile unit and could be suspended internally of the vessel 1, in an elevated position relative to the solid line position externally of the vessel, thereby to suspend the casters 26A even if the sterilizer floor 4 is at the same level 11 as the room floor 10. However, in the illustrated embodiment the suspended mobile unit 18A rests in a final position at the same level as the solid line position externally of the vessel due to the fact that the central roller 30 is received in a detent 36 formed in the track 28 and the two outside rollers engage a lower portion of the elevating cam surfaces 34 of the leading and trailing edges of the mobile unit.

While it is not essential of the concept of my invention in its broadest aspect, it is a significant improvement that I provide the detent 36 thereby to secure the suspended mobile unit 18 in the desired position internally of the vessel.

Suspending the mobile unit 18 internally of the vessel so that it does not engage the sterilizer floor 4 is desirable so that flats will not be imparted to the tires of the casters 26 as a result of resting on the floor 4 and being subjected to heat when the vessel 1 is under steam pressure during the sterilizing cycle.

Thus, I provide an invention which eliminates the ramp otherwise necessary for moving the mobile unit into the vessel. My invention suspends the mobile unit internally of the vessel to relieve pressure on the casters. The support elements 30 internally of the vessel and support elements on tracks 28 on the mobile unit serve to position the mobile unit within the vessel both laterally and longitudinally.

While there is hereinabove described the preferred forms of this invention it will be apparent that various modifications and changes may be made therein, without departing from the spirit of this invention as set forth in the appended claims.

I claim:
1. In combination:
   a. a sterilizing vessel enclosing a sterilizing chamber and having a vessel floor;
   b. a mobile unit having a plurality of wheel means for rollably supporting said unit on a floor, said mobile unit having a size such that it can be fully received with said wheel means into said chamber, said wheel means being deformable when subjected in said chamber simultaneously to the weight of a loaded mobile unit and to heat;
   c. first support means fixedly mounted in said vessel for supporting said mobile unit in said chamber in a completely suspended position with said wheel means off of said vessel floor, whereby said wheel means will not become deformed;
   d. the tops of said first support means being spaced above said vessel floor a sufficient distance to hold said wheel means of said mobile unit up off of said vessel floor when said mobile unit is received within said chamber;
   e. means on said mobile unit for supporting articles to be sterilized in said chamber; and
   f. second support means mounted on said mobile unit for contacting and being received on said first support means when said mobile unit is positioned within said chamber.
2. The apparatus according to claim 1 wherein
   a. said sterilizing vessel includes vessel sidewalls, a top wall, and said vessel floor for enclosing said sterilizing chamber, and and opening through one of said sidewalls into said chamber;
   b. a floor including a recess within which said vessel is mounted and having an open channel directly in front of said opening, said channel having a fixed, predetermined width between said floor and said sterilizing vessel; said vessel floor and said floor being at approximately the same level;
   c. forward projection means mounted on said mobile unit at at least one end thereof for contacting said first support means as said mobile unit is being rolled through said opening and into said chamber and prior to the adjacent wheel means reaching said channel and for lifting up the corresponding end of said mobile unit off of said adjacent wheel means; and d. said forward projection means being located adjacent said second support means such that as said mobile unit moves into said chamber, support for said mobile unit by said first support means is transferred from said forward projection means to said adjacent second support means.

3. The apparatus according to claim 2 wherein:
a. said first support means is mounted on said vessel floor and comprises two parallel, spaced apart, rows of support means, each row being perpendicular to the plane of the vessel wall in which said opening is located;
b. said second support means includes track means and said track means comprises a pair of parallel rows of tracks, spaced apart approximately the same distance as are said rows of support means;
c. said forward projection means comprise terminal portions of said track means; and wherein,
d. said forward projection means terminate in an upwardly tapering elevating cam surface.

4. The apparatus according to claim 3 including:
a. mating detent means on said pair of tracks for contacting said first support means:
b. said first support means comprising anti-friction rollers; and
c. said pair of tracks being mounted to the bottom of said mobile unit and extending substantially the entire length of said mobile unit and being positioned outwardly from said wheel means.

* * * * *